United States Patent [19]
Malmin

[11] 3,949,479
[45] Apr. 13, 1976

[54] ENDODONTIC OPERATING AND SEALING METHOD AND APPARATUS THEREFOR

[76] Inventor: Oscar Malmin, 127 E. Wayne Ave., Akron, Ohio 44301

[22] Filed: Aug. 1, 1974

[21] Appl. No.: 493,509

Related U.S. Application Data

[63] Continuation of Ser. No. 305,973, Nov. 13, 1972, Pat. No. 3,855,702.

[52] U.S. Cl. ................................................. 32/15
[51] Int. Cl.² ......................................... A61K 5/02
[58] Field of Search ........................ 32/15, 40 R, 57

[56] References Cited
UNITED STATES PATENTS

| | | | |
|---|---|---|---|
| 1,312,120 | 8/1919 | Hurtt | 32/15 |
| 1,463,963 | 8/1923 | Miller | 32/15 |
| 3,675,329 | 7/1972 | Weissman | 32/15 |
| 3,855,702 | 12/1974 | Malmin | 32/15 |

*Primary Examiner*—Robert Peshock
*Attorney, Agent, or Firm*—Freeman & Taylor

[57] ABSTRACT

An endodontic operating and sealing or obturating method and apparatus for performing the various steps of said method are disclosed. Means for preparing a root canal for filling are disclosed which include instruments for cleaning out the root canal and preparing the interior of the canal so that it includes a series of staged steps which grow progressively larger from the apical end of the tooth to the crown. Unique finishing instruments are provided with a cross-sectional configuration such that they will provide the progressively larger steps. Also disclosed is a method and apparatus for sealing the root canal thus prepared, which includes provision of the gutta percha cones of particular configuration adapted to substantially conform to the internal stepped configuration within the root canal. Also disclosed is a combination cone which in itself is composed of a series of cones having progressively increasing diameters so as to be capable of sealing a plurality of steps in the canal. Improved means for inserting the cones into the root canal and assuring complete sealing thereof are also provided.

2 Claims, 21 Drawing Figures

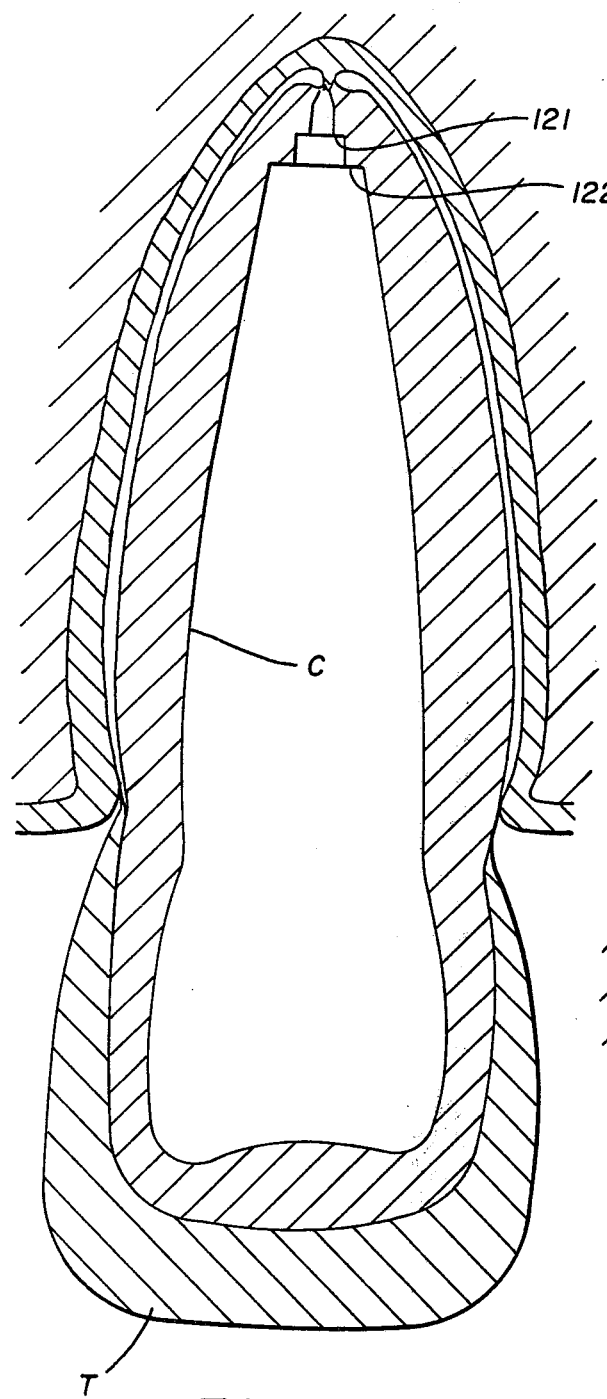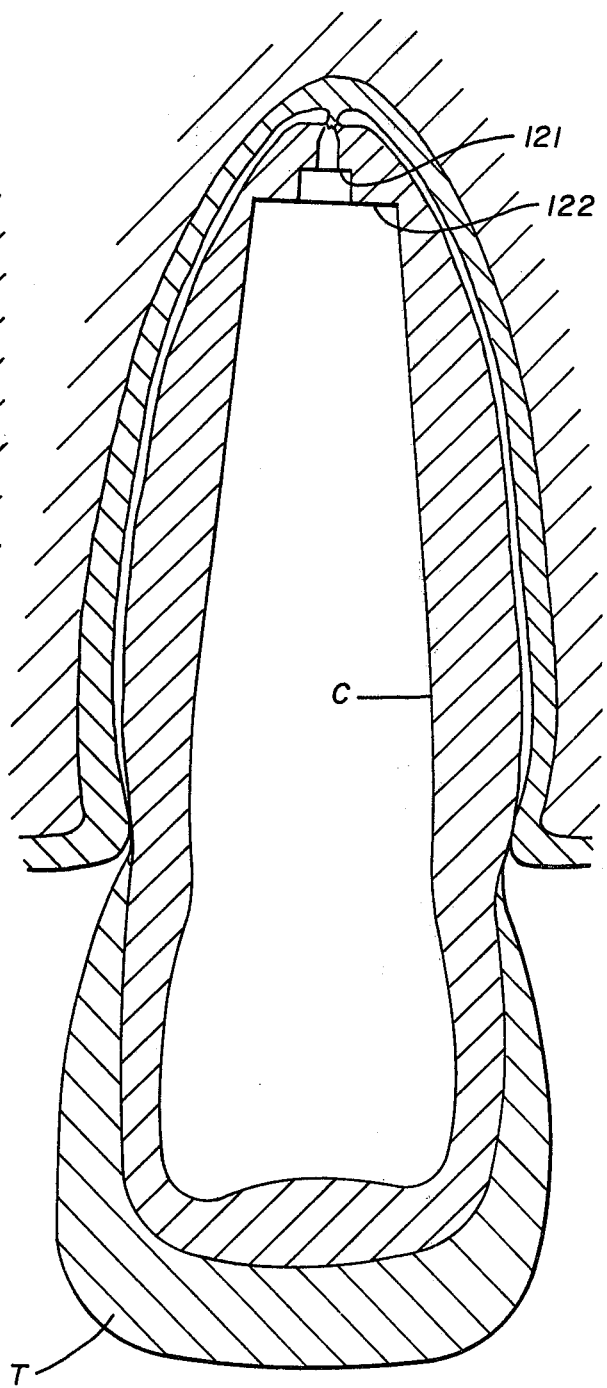

ENDODONTIC OPERATING AND SEALING METHOD AND APPARATUS THEREFOR

RELATED APPLICATIONS

This application is a continuation of Applicant's earlier filed application Ser. No. 305,973 filed Nov. 13, 1972 and now U.S. Pat. No. 3,855,702 issued Dec. 24, 1974, entitled "Improved Endodontic Operating and Sealing Method and Apparatus Therefor." This application is also an improvement on and an expansion of the principles set forth in Applicant's earlier U.S. Pat. No. 3,772,791 entitled "Endodontic Operating System" and Applicant's earlier patent application entitled "Endodontic Sealing System and Apparatus" filed Dec. 30, 1971, as Ser. No. 213,993.

BACKGROUND OF THE INVENTION

This invention, in general, relates to an endodontic root canal preparation method and the apparatus therefor, as well as to an endodontic sealing method to be operated in conjunction with the operating method and again the apparatus for carrying out the method.

DESCRIPTION OF THE PRIOR ART

The following patent prior art is known to Applicant:

| Low | U.S. Patent | 376,603 |
| --- | --- | --- |
| Kinsman | U.S. Patent | 674,419 |
| Lederle | U.S. Patent | 1,013,666 |
| Siegel | U.S. Patent | 1,757,595 |
| Siegel | U.S. Patent | 3,358,826 |
| Saffro | U.S. Patent | 3,562,913 |
| Weissman | U.S. Patent | 3,675,329 |

In addition to the aforementioned patent prior art, Applicant is aware of various forms of pluggers or applicators for endodontic sealing work, as well as reamers, broaches, etc., for preparing root canals. None of the devices known to Applicant has the capability of providing complete sealing with the consistency, reliability, and accuracy of the method disclosed herein.

SUMMARY OF THE INVENTION

It has been found that the preferred method of internal preparation of a root canal of a tooth and the preparation of that canal so as to obtain the highest possible degree of total obturation based upon the anatomical form can be achieved by first preparing the root canal in conventional fashion with a broach and a reamer which gives a tapered effect to the canal.

It has then been discovered that by providing a series of progressively larger cross-sectional finishing instruments, it is possible, beginning at the apical end of the tooth, to provide a series of steps or progressively larger diameter ledges toward the crown of the tooth. Such ledges differ from conventional forms of preparation in that force is distributed laterally, thereby sealing accessory canals rather than exerting full pressure in the apical foramen thereby extruding filling materials into the tissues surrounding the tooth.

It has further been found that once the root canal has been prepared in this fashion, improved sealing and obturation can be achieved by providing cones of gutta percha or similar material which substantially conform to the internal configuration of the canal once it has been prepared as above-noted.

It has been found that this can be accomplished either by utilizing a plurality of progressively larger cones or by using a unique combination cone which is unitary but has progressively larger diameters thereon.

It has also been found that placement of the cones can be improved by providing them with an integral wire member or shank, and unique placement and separation forceps can be utilized to implace the cones, following which appropriate ultrasonic condensing instruments such as disclosed in Applicant's co-pending application, Ser. No. 213,993, can be used to obtain the greatest possible degree of obturation.

Accordingly, production of an improved endodontic operating and sealing method and apparatus therefor becomes the principal object of this invention, with other objects thereof becoming more apparent upon a reading of the following brief specification and claims considered and interpreted in view of the accompanying drawings.

Figure 4:
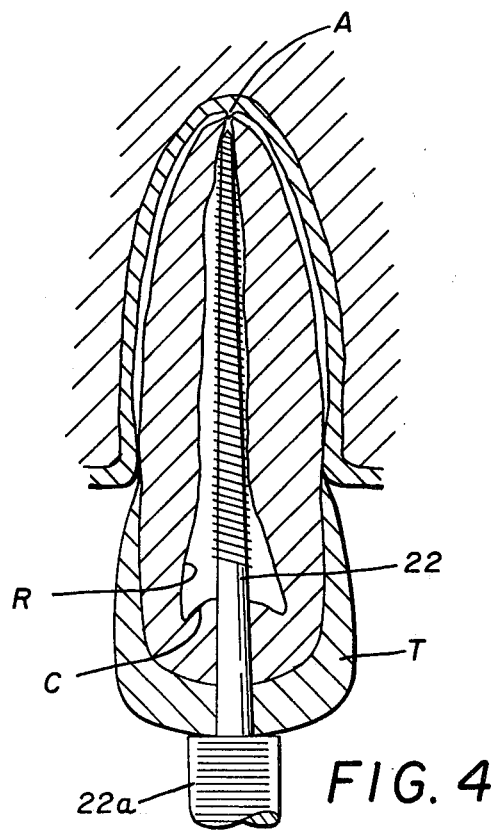

FIG. 4 is a similar cross-sectional view showing a reamer similar to that disclosed in Applicant's earlier U.S. Pat. No. 3,713,221.

Figure 5:
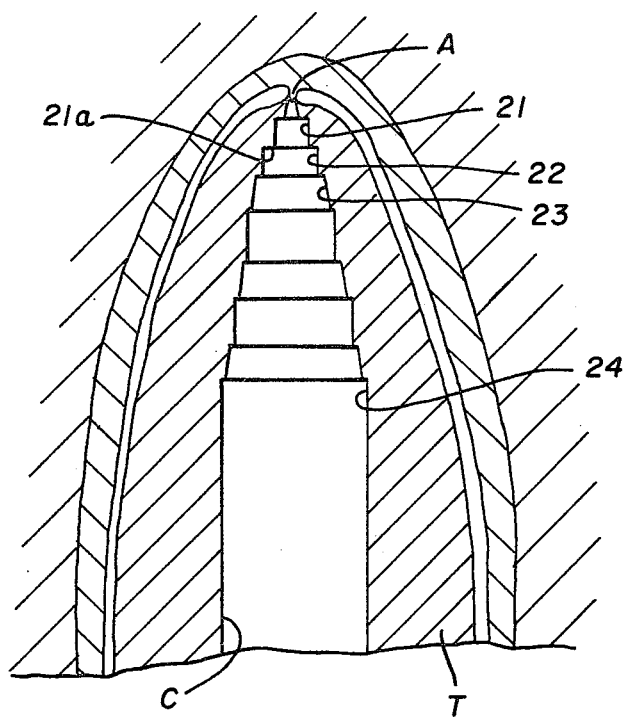

FIG. 5 is a cross-sectional view showing a root canal which has been prepared in staged steps in accordance with the teachings of the invention.

Figure 6:
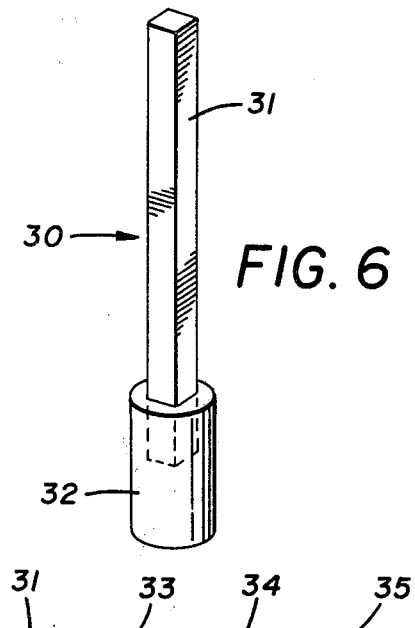

FIG. 6 is a perspective view of an apical finishing tool such as would be utilized to prepare the canal as shown in FIG. 5.

Figure 7:
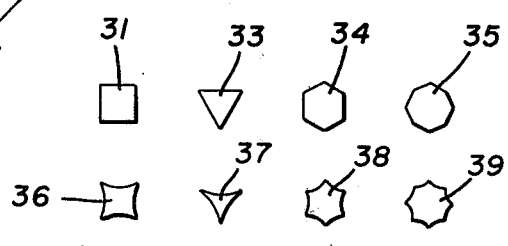

FIG. 7 shows a plurality of possible alternative cross sections for the instrument of FIG. 6.

Figure 8:
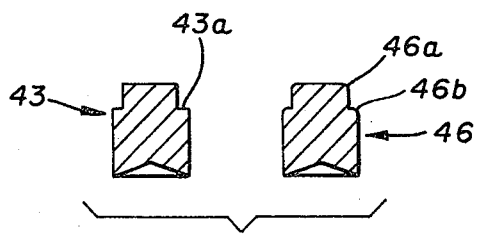

FIG. 8 is a cross-sectional view of gutta percha cones intended to be utilized in conjunction with the present invention.

Figure 9:
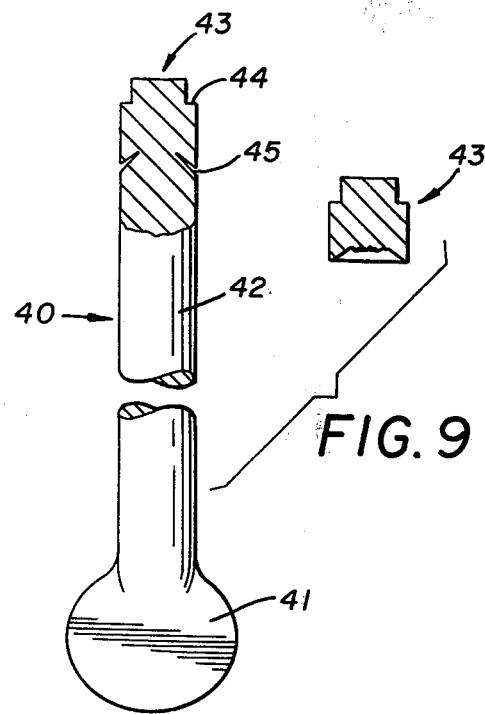

FIG. 9 shows a typical hand-operated type of gutta percha cone which can be used in a root canal prepared in accordance with the teachings of this invention.

Figure 10:
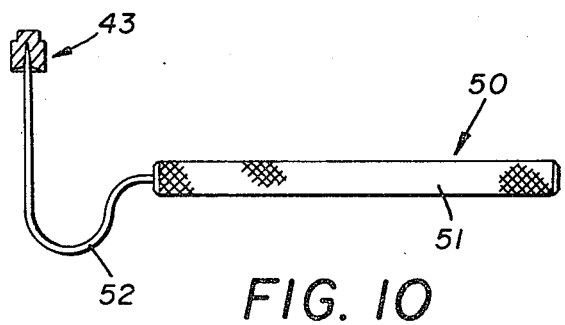

FIG. 10 is an elevational view showing one of the cones of FIG. 8 and an instrument for inserting or placing the same.

Figure 11:
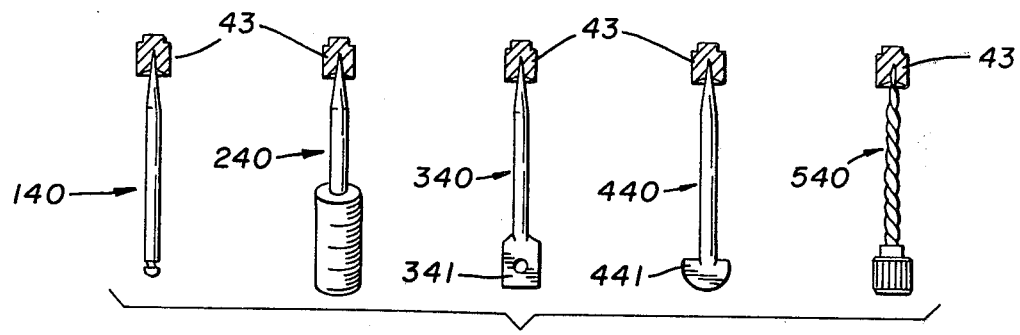

FIG. 11 is an elevational view showing a plurality of variations for cones such as shown in FIG. 8.

Figure 12:
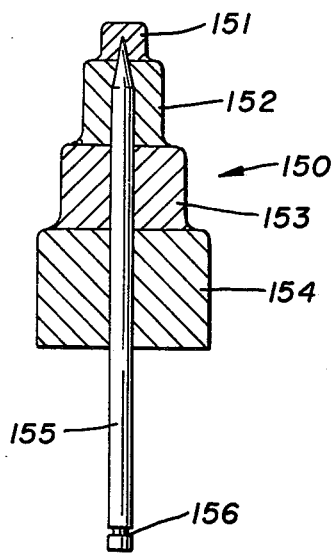

FIG. 12 is a cross-sectional view of a combination cone in elevation which has a plurality of different diameters.

Figure 13:
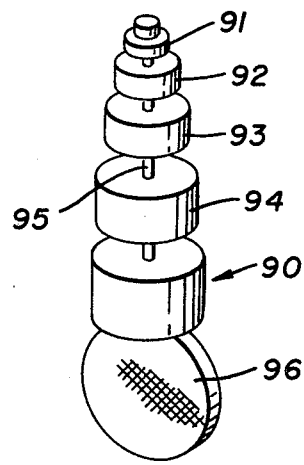

FIG. 13 is a perspective view of a variation of the combination cone.

Figure 14:
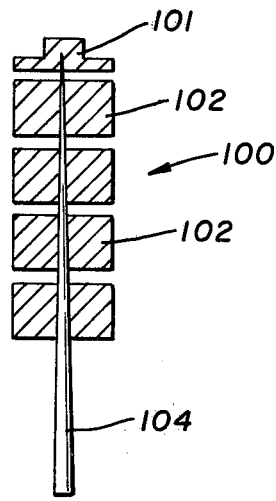

FIG. 14 is a cross-sectional view of a modified combination cone.

Figure 15:
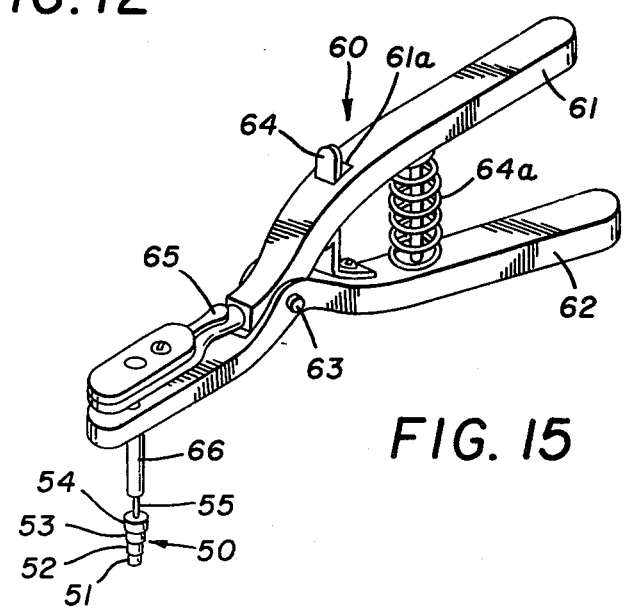
Figure 16:
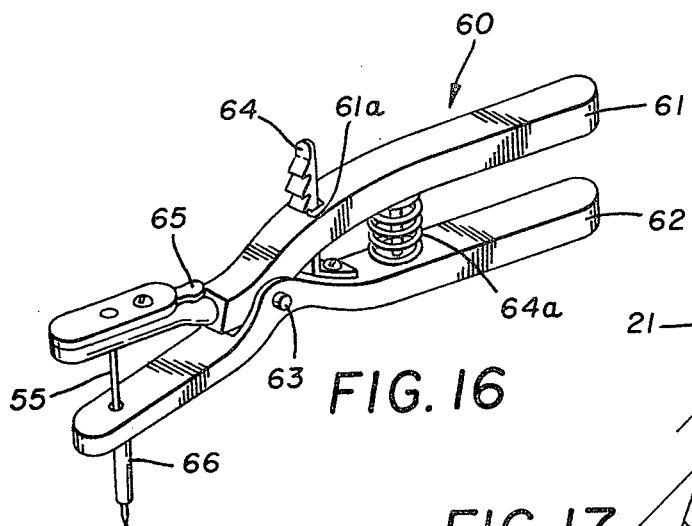

FIGS. 15 and 16 are perspective views of applicator forceps adapted to locate cones such as shown in FIGS. 11, 12, and 14 in the root canal.

Figure 17:
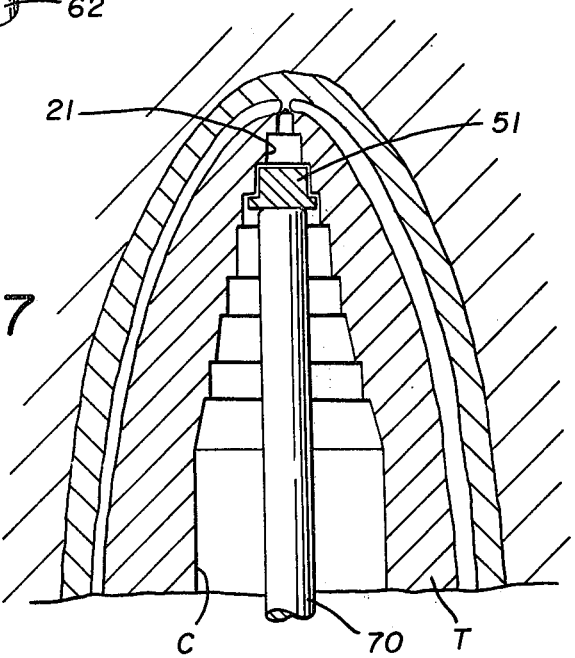

FIG. 17 is a cross-sectional view of the first step of the sealing operation with one mini-cone in position and an ultrasonic condensing instrument applied thereto.

Figure 18:
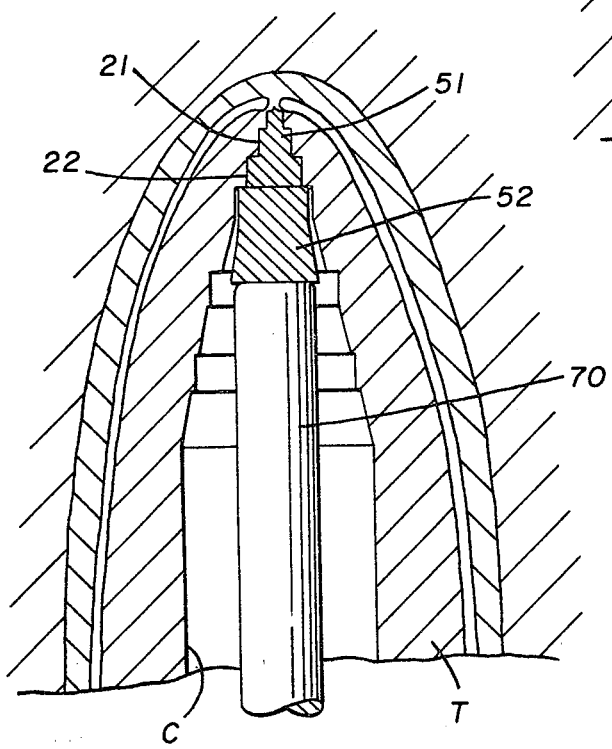

FIG. 18 is a view similar to FIG. 17 showing a still further progression of the sealing process.

Figure 19:
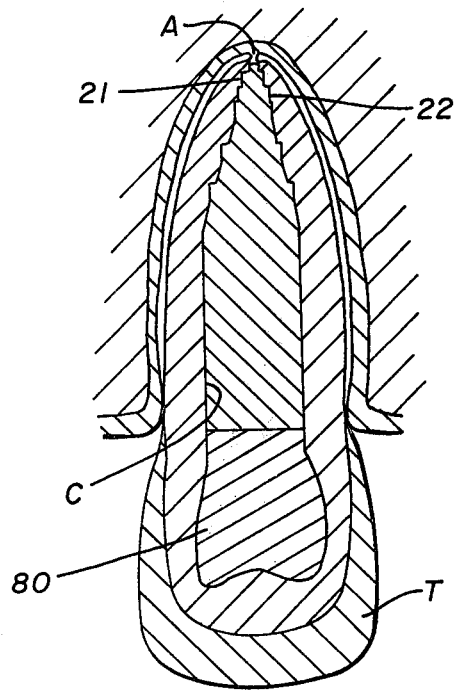

FIG. 19 is a cross-sectional view which shows the tooth with the root canal completely obturated by use of the cones.

FIGS. 20 and 21 are cross-sectional views showing a root canal prepared in a modified fashion.

BRIEF DESCRIPTION OF THE PREFERRED EMBODIMENTS

Figure 1:
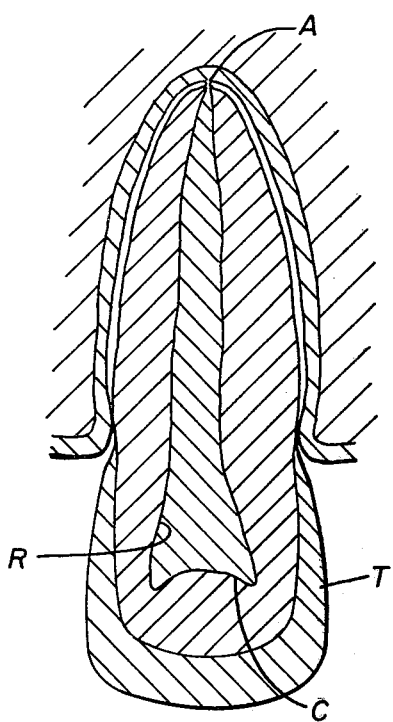
FIG. 1 is a cross-sectional view of a tooth showing a typical root canal.

Turning first then to FIG. 1, it will be noted that FIG. 1 illustrates a sectional view of a typical tooth T having a root canal R therein. The canal R stretches from its apical end A to its coronal end C.

The method of treatment disclosed is perhaps best explained by a step-by-step approach, and accordingly FIG. 1 shows the tooth before treatment, with subsequent views illustrating the steps of the method and the instrumentation for carrying it out.

Figure 2:
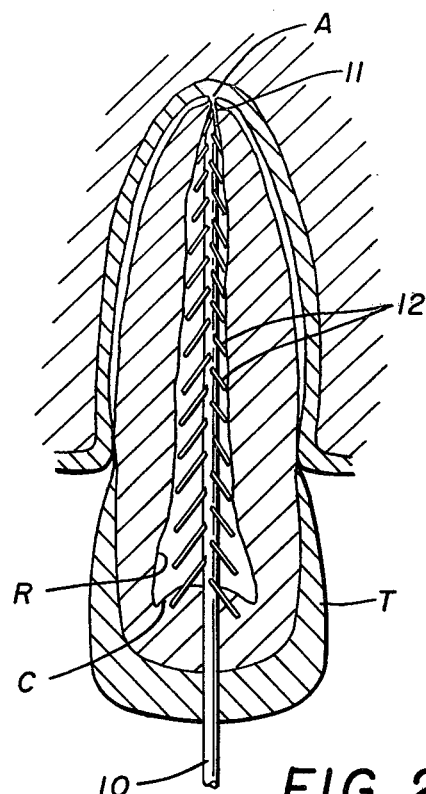
FIG. 2 is a cross-sectional view similar to FIG. 1 showing a broach in place within the tooth.

Turning next to FIG. 2, the tooth of FIG. 1 is shown with a conventional broach 10 inserted therein. This broach 10 will have a barb-like operative end 12 and an apical end 11 and will be utilized initially to remove the pulp or remaining pulp remnants in a gross manner and to roughly finish the interior of the root canal R.

Figure 3:
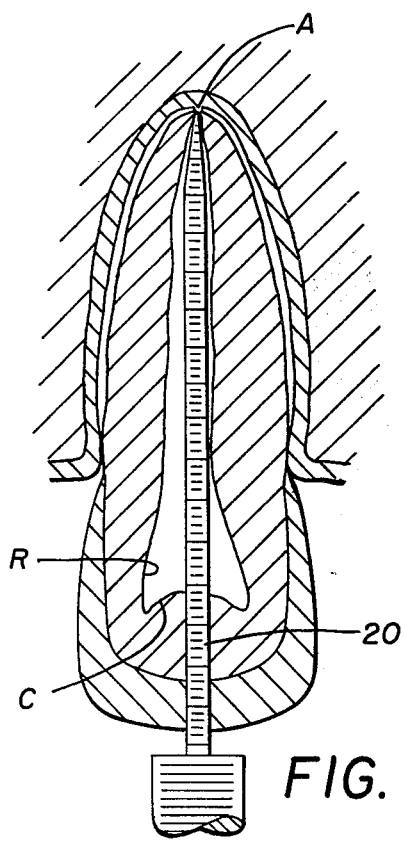
FIG. 3 is a view similar to FIGS. 1 and 2 showing a measurement instrument such as disclosed in Applicant's earlier U.S. Pat No. 3,772,791, referred to above.

FIG. 3 illustrates the same tooth T with a measurement instrument 20 such as illustrated in Applicant's earlier U.S. Pat. No. 3,772,791. The measurement method and apparatus is fully disclosed in that patent, but it should be noted that once the measurement instrument is inserted, an X-ray is taken to determine the working length desired for the root canal. Once this length has been determined, a reamer 22, such as shown in FIG. 4, will be employed with a stop 22a, as disclosed again in Applicant's earlier patent, being applied to the head. As pointed out in that patent, once the stop is secured to the head, it will bottom on the crown of the tooth and limit the working length of the root canal as predetermined.

It should be understood that the smallest diameter reamer is used initially and that a plurality of progressively larger diameter reamers will be used until resistance to the reaming action is observed by the dentist. At that time the operation of the reamer will be continued until all resistance to the largest instrument utilized has been removed. Thus the canal will have been opened and cleaned and will have a fairly uniform taper from a largest dimension at the coronal portion of the canal to a narrowest dimension at the apical end thereof.

Turning next then to FIGS. 5 and 6 for the next step in the method, it will be noted that an apical finishing instrument 30 is disclosed. This instrument has a blade 31 and a handle 32. In the form illustrated in FIG. 6 the cross sectional configuration of the blade is substantially square. FIG. 7, however, illustrates alternatives such as triangular in 33, hexagonal in 34, octagonal in 35. Also, while the instruments 30, 31, 33, 34, and 35 are illustrated as having straight side walls, it is possible to undercut the walls of the various cross-sectional instruments as shown in 36, 37, 38, and 39 by hollow grinding them. It should also be noted that the cross-sectional configurations illustrated are for the sake of illustration only and are not intended to be exhaustive.

Referring again then to FIG. 5, it will be noted that FIG. 5 shows the end result of utilization of apical finishing instruments such as 30. Thus it will be seen that starting at the apical end A of the canal, a series of progressively larger steps 21, 22, 23, 24 are provided.

Thus in operation the canal would be prepared as shown in FIGS. 1 through 4 by use of conventional instruments.

Following this, the smallest diameter apical finishing instrument 30, which corresponds in diameter to the last reamer used, would be inserted into the canal and utilized to create the first staged step indicated at 21 and which may be called the apical seal step. It should be noted that this first step will be spaced from the ultimate apical end A of the canal as shown in FIG. 5, with this distance normally being about one millimeter from the end of the working length established by the measurement instrument shown in FIG. 3.

Following this, succeeding steps 22, 23, for example, are obtained by utilizing progressively larger diameter instruments such as 30. In this regard only one size has been illustrated, with it believed to be apparent that greater diameters could be provided. In this fashion a series of progressively larger openings are provided throughout the length of the canal creating a ledge or step at each stage and ultimately ending at the widest diameter, as indicated at 24.

In practice, starting with the first step at 21, each succeeding step is created by withdrawing three millimeters and reaming the canal to a successively larger diameter, although precise measurements do not form a part of the invention with that depending upon the anatomy of the root canal system and the operator's preference.

The end result will be to provide a root canal prepared along the lines shown in FIG. 5. It should also be noted that the widths in question have been exaggerated for purposes of illustration, with it being understood that all of the components are considerably exaggerated for that purpose also. The advantage of this final intra-radicular preparation form is that positive ledging serves to transfer force laterally thereby sealing lateral or accessory canals more effectively than present preparation forms. Further, such positive ledging serves to avoid the entire condensing or filling force from forcing the filling materials through the apical foramen and into the surrounding tissues with resulting irritation and pain that commonly occurs in present methods.

FIGS. 8 and 10 illustrate one method of doing this. Thus FIG. 8 shows a gutta percha plug 43 having a stepped end at 43a. FIG. 8 also shows a slight variation of this in which the corners are rounded as at 46a and 46b.

When utilizing this type of cone or plug, it is simply necessary to use the hand instrument 50 by grasping the handle 51 and inserting the projecting end 52 into the cone. At this time the cone would be placed into the first staged step or apical seal step 21. At that point, suitable condensing devices as shown in Applicant's co-pending application, Ser. No. 213,993, could be utilized to tamp the plug 43 in place and assure complete obturation of the primary canal and the lateral canals. In this regard the cone would have a slightly smaller dimension than that of the step 21 which would be compensated for by the condensing and packing operation.

FIG. 11 also shows other means for implacing the mini-cone in the prepared canal. Thus the numeral 140 indicates a cone of the type shown in FIG. 8, which has a wire embedded therein and would be suitable for use with the handle means disclosed in Applicant's earlier U.S. Pat. No. 3,713,221.

The numeral 240 indicates a different form of the invention in which a handle and stopping mechanism, such as shown in Applicant's earlier U.S. Pat. No. 3,772,791 are employed.

The numeral 340 indicates formation of a handle by crushing or flattening the projecting wire at 341 to provide a gripping surface.

To the same effect, 440 indicates a conventional nail, brad, or pin with an enlarged head 441 which would facilitate gripping.

Finally, 540 indicates application of the cone by utilizing a conventional root canal reamer as a mechanism for implacing the miniature cone in the root canal.

It is also possible to use a cone such as shown in FIG. 9 where the device 40 has an elongate body 42, an enlarged head 41, and a cone portion 43. Portion 43 has a configuration matching apical step 21 and is connected to body 42 by a thin neck formed by cutting an annular groove 45 in the body. Once the apical cone is in place, the body is twisted so that it breaks at the neck leaving the cone 43 in place.

Once the apical seal cone is in place, utilization of a plurality of increasing diameter cones of the general types shown in FIGS. 8, 10, and 11 will result in ultimately filling the root canal. It has been found that further improved results can be obtained by utilizing a fully integrated combination cone such as shown in FIG. 12. Thus in FIG. 12 such a cone 150 is composed of a series of cones which have a progressively increasing diameter, going from the smallest diameter at 151 to the largest at 154, with these diameters corresponding to the steps in the root canal prepared as shown in FIG. 5. An elongate handle 155 is provided of some rigid material, with a groove 156 provided on its outboard end to be engaged by the forceps shown in FIGS. 15 and 16 which will be described later.

Thus in order to utilize this type of cone, forceps 60 will be employed. The forceps include a pair of opposed handles 61, 62 pinned as at 63 and interconnected by spring 64a so that they would normally be urged to the position of FIG. 15. The handle 61 has an opening 61a thereon, and a latch 64 is secured to the handle 62 and projects through the opening 61a so that the forceps can be locked in any predetermined position.

Provided on the forward end of the forceps is a locking latch 65 with a separating tube 66. It will be noted that the shank 55 of the cone 50 has been secured in place. When it is desired to insert the cone 50 in the tooth, it is merely necessary to insert it into the canal, following which the handles 61 and 62 are brought together against the force of the spring 64a. At this point the separating tube 66 will force the endmost cone off the handle 55 and into place in the tooth, following which condensing by the normal ultrasonic instruments is accomplished as described above.

It will also be noted that latch 64 has a plurality of teeth thereon which engage the edge of opening 61a so that by correlating the spacing of the teeth to the depth of cones 51, 52, 53, and 54, compression of the handles and successive engagement of the teeth will dislodge the individual cones as required.

FIGS. 17 and 18 show progressive steps of the sealing method. Thus FIG. 17 shows the apical sealing cone which could be the form shown in FIGS. 9 and 10 or the form shown in FIG. 12. The apical cone has been placed in place in the first step 21, and the condensing point 70 is being applied to it.

In FIG. 18 condensing of the first cone has been completed, and it will be noted that while the cone is initially slightly undersized with relation to the step 21, the condensing action spreads it so that it does, in fact, fill the space. In FIG. 18 the second cone, such as 52, has been inserted, and again condensing head 70 is being applied thereto.

FIG. 19 shows a completed root canal in which all of the successively larger cones have been separately implaced and condensed so that the entire canal structure is completely obturated. Following this, of course, the appropriate sealing or filling material 80 would be implaced in the coronal portion of the tooth, following which the root canal therapy will have been completed.

FIGS. 13, 14, 20, and 21 illustrate an alternative and more simplified methods of sealing root canals.

Thus while the method shown above is satisfactory and would, in fact, be the ideal method of obturating a root canal system, it has been discovered that an even more simplified method could be employed which would result in a saving of time and effort and thereby increase the efficiency of the operator.

Thus referring to FIGS. 20 and 21 and assuming that the root canal had first been prepared as shown in FIGS. 1 through 4 and described above, the first step would be to apply the apical finishing instrument, such as shown in FIG. 6, to provide the first or apical seal step 121. The second step 122, however, would be prepared by using the largest diameter instrument which would provide an uninterrupted root canal preparation from the level of the step 122 to the coronal portion or opening of the tooth.

When this form or preparation is utilized, it is possible to employ different cone constructions.

Thus referring to FIG. 13, it will be seen that a modified combination cone 90 is employed which has an apical sealing cone 91 and a plurality of additional cones 92, 93, 94, each of which is interconnected by a relatively thin central core 95 of gutta percha and has a grasping portion 96 at the opposed end. This type of cone makes it possible to insert, for example, the apical cone 91 into place, and then by twisting, the thin core 95 will be broken. Following this, the condensing operation can take place and then the cone 92 will be implaced and a similar operation will ensue until all of the cones have been implaced and condensed.

FIG. 14 shows yet another form of combination cone 100 with an apical finishing member 101 and a plurality of cones 102,102. The cones are all connected by a central metal core pin 104. In this way again the apical cone 101 is implaced, and the device is withdrawn, following which the condensation operation takes place and the sequence of events is similar to that described above.

It should be noted that the walls of the canal shown in FIGS. 17 and 18 are tapered from a minimum diameter adjacent step 121 to a maximum diameter at the coronal end.

Depending upon the configuration of the finishing instrument 30, these walls could also be straight. A similar difference will be noted between the combination cones 90 and 100 shown in FIGS. 13 and 14 in which in FIG. 13 the cones are of increasing diameter to accommodate a canal which has been prepared with an increasing diameter, while in FIG. 14 the cones are of identical diameter as would be the case when the walls of the canal are parallel.

While a full and complete description of the invention has been set forth in accordance with the dictates of the Patent Statutes, it should be understood that modifications can be resorted to without departing from the spirit hereof or the scope of the appended claims.

What is claimed is:

1. A substantially compressible gutta percha endodontic sealing member for use in root canals comprising; an elongate removable handle portion; gripping means disposed on one end of said handle portion; an integral elongate body portion projecting from the opposed end of said handle; the projecting end of said body terminating in a reduced diameter portion to form an offset annular shoulder thereon and having a length dimension substantially shorter than the length dimension of said root canal; and said body portion having a circumferential weakening slot adjacent to said projecting end whereby said projecting end may be separated from said body following insertion of said sealing member into said root canal.

2. A substantially compressible gutta percha endodontic sealing plug for use in root canals, comprising a short stubby cylindrical body having a base end and an opposed end with an offset reduced diameter projection thereon which forms an annular shoulder adjacent said opposed end, said body having a length dimension substantially shorter than the length dimension of said root canal; a removable rigid handle frictionally engaging said body of said plug and having one end projecting from the base of said plug; and gripping means disposed on the opposed end of said handle.

* * * * *